US006860143B2

(12) United States Patent
Yamazaki et al.

(10) Patent No.: US 6,860,143 B2
(45) Date of Patent: Mar. 1, 2005

(54) STATE DETERMINING APPARATUS FOR HUMIDITY SENSOR

(75) Inventors: Hideharu Yamazaki, Saitama-ken (JP); Masahiro Sato, Saitama-ken (JP); Kei Machida, Saitama-ken (JP); Takashi Haga, Saitama-ken (JP); Masaki Ueno, Saitama-ken (JP)

(73) Assignee: Honda Giken Kogyo Kabushiki Kaisha, Tokyo (JP)

(*) Notice: Subject to any disclaimer, the term of this patent is extended or adjusted under 35 U.S.C. 154(b) by 0 days.

(21) Appl. No.: 10/232,723

(22) Filed: Sep. 3, 2002

(65) Prior Publication Data

US 2003/0046979 A1 Mar. 13, 2003

(30) Foreign Application Priority Data

Sep. 3, 2001 (JP) ........................................ 2001-265448
Jul. 18, 2002 (JP) ........................................ 2002-209638

(51) Int. Cl.$^7$ ........................ G01M 19/00; G01N 19/10; G01N 7/00; F01N 7/00; F01N 3/00
(52) U.S. Cl. .................... 73/118.1; 73/29.02; 73/29.01; 60/277; 60/284
(58) Field of Search ........................ 73/118.1, 170.29, 73/863.33, 30.02; 60/277, 297; 204/424, 412; 62/94; 429/13

(56) References Cited

U.S. PATENT DOCUMENTS 4,379,406 A * 4/1983 Bennewitz et al. ........ 73/336.5
5,687,692 A * 11/1997 Togai et al. ................ 123/436
5,968,452 A * 10/1999 Silvis ........................... 422/62
6,422,006 B2 * 7/2002 Ohmori et al. ............... 60/297
6,477,830 B2 * 11/2002 Takakura et al. ............. 60/277

FOREIGN PATENT DOCUMENTS

| EP | 1 203 878 A2 | 5/2002 |
| JP | 2001-323811 | 11/2001 |
| JP | 2002-004842 | 1/2002 |
| JP | 2002-004846 | 1/2002 |

OTHER PUBLICATIONS

Search Report dated Nov. 7, 2002.

* cited by examiner

*Primary Examiner*—Edward Lefkowitz
*Assistant Examiner*—Octavia Davis
(74) *Attorney, Agent, or Firm*—Westerman, Hattori, Daniels & Adrian, LLP (57) ABSTRACT

A state determination apparatus for a humidity sensor is provided for accurately determining the state of the humidity sensor, including the responsibility, from a result detected by the sensor itself. The state determining apparatus is configured to determine a humidity sensor arranged in an exhaust system of an internal combustion engine for detecting a humidity within an exhaust pipe. The apparatus comprises an ECU which determines whether or not the internal combustion engine is in a predetermined operating condition, calculates a change state parameter indicative of a change state of a value detected by the humidity sensor based on the detected value of the humidity sensor detected when the internal combustion engine is in the predetermined operating condition, and determines the state of the humidity sensor in accordance with the calculated change state parameter.

4 Claims, 8 Drawing Sheets

STATE DETERMINING APPARATUS FOR HUMIDITY SENSOR

BACKGROUND OF THE INVENTION

1. Field of the Invention

The present invention relates to a state determining apparatus for determining the state of a humidity sensor arranged in an exhaust system of an internal combustion engine for detecting the humidity within an exhaust pipe.

2. Description of the Prior Art

The applicant has already proposed a state determining apparatus for a humidity sensor of the type mentioned above, for example, in Laid-open Japanese Patent Application No. 2001-323811. The humidity sensor is arranged at a location downstream of an adsorbent for adsorbing hydrocarbons contained in exhaust gases in order to determine a deterioration of the adsorbent. The determination on the deterioration of the adsorbent relies on the characteristic of the adsorbent made of zeolite or the like that adsorbs moisture simultaneously with hydrocarbons, and on a proportional relationship of the ability to adsorb hydrocarbons to the ability to adsorb moisture. Thus, the humidity of exhaust gases after passing through the adsorbent is detected by the humidity sensor to determine a degradation in the ability of the adsorbent to adsorb moisture, i.e., a deterioration of the adsorbent. Specifically, the state determining apparatus sets a predetermined time required for the humidity detected by the humidity sensor to rise by a predetermined value, associated with a gradual rise in the humidity of exhaust gases passing through the adsorbent which adsorbs moisture in the meantime after the start of an engine in accordance with the humidity at the time of the start, and the like, and measures an actual time taken for the detected humidity to rise by the predetermined value. Then, the state determining apparatus determines that the adsorbent is deteriorated when the measured time is shorter than the predetermined time, from the fact that the detected humidity rises at a high rate.

While a deterioration of the adsorbent is determined based on the result detected by the humidity sensor as described above, a sensing element, which forms part of the humidity sensor, is exposed at all times to exhaust gases at high temperatures and therefore highly susceptible to deterioration. Since the deteriorated humidity sensor could adversely affect the accuracy of the deterioration determination on the adsorbent, an additional failure determination (state determination) is made for the humidity sensor together with the deterioration determination for the adsorbent. The failure determination for the humidity sensor relies on the fact that a value detected by the humidity sensor stably remains substantially at a constant value in a high humidity region when the adsorbent has completely adsorbed hydrocarbons and moisture in exhaust gases and is saturated. The humidity sensor is determined to be at failure when the humidity detected by the humidity sensor at a timing at which the adsorbent is estimated to be saturated is lower than a predetermined value.

However, the foregoing technique for determining a failure in the humidity sensor merely compares the humidity detected by the humidity sensor, which remains substantially at a constant value due to the saturated adsorbent, with the predetermined value. For this reason, for example, even when the humidity sensor is deteriorated with a lower responsibility which causes the detected humidity during adsorption of the adsorbent to actually change at a very low rate, the humidity sensor is determined as normal when the detected humidity eventually reaches the predetermined value. On the other hand, in the deterioration determination for the adsorbent, the adsorbent is determined as deteriorated when the humidity detected by the humidity sensor during adsorption rises at a high rate, as described above. Thus, when a deteriorated humidity sensor with a low responsibility is used for determining a deterioration of an adsorbent, the adsorbent, which is actually deteriorated, could be erroneously determined as normal because the detected humidity rises at a lower rate during adsorption, giving rise to a reduction in the accuracy of the deterioration determination for the adsorbent.

OBJECT AND SUMMARY OF THE INVENTION

The present invention has been made to solve the problem as mentioned above, and it is an object of the invention is to provide a state determination apparatus for a humidity sensor which is capable of accurately determining the state of a humidity sensor, including the responsibility, from a result detected by the sensor itself.

To achieve the above object, the present invention provides a state determining apparatus for a humidity sensor arranged in an exhaust system of an internal combustion engine for detecting a humidity within an exhaust pipe. The apparatus is characterized by comprising operating condition determining means for determining whether or not the internal combustion engine is in a predetermined operating condition; change state parameter calculating means for calculating a change state parameter indicative of a change state of a value detected by the humidity sensor based on the detected value of the humidity sensor detected when the internal combustion engine is in the predetermined operating condition; and state determining means for determining the state of the humidity sensor in accordance with the calculated change state parameter.

According to this state determining apparatus for a humidity sensor, a change state parameter indicative of a change state of a value detected by the humidity sensor is calculated based on the detected value of the humidity sensor detected when the internal combustion engine is in the predetermined operating condition, and the state of the humidity sensor is determined in accordance with the calculated change state parameter. Thus, the change state parameter reflects a change situation of the value actually detected by the humidity sensor during a predetermined operating condition of the internal combustion engine, so that the state determining apparatus for a humidity sensor can appropriately determine the characteristics and/or state of the humidity sensor, including the responsibility, in accordance with the operating condition of the internal combustion engine in accordance with the change state parameter.

Preferably, the state determining apparatus for a humidity sensor further comprises an adsorbent capable of adsorbing hydrocarbons and moisture in exhaust gases, and arranged at a location upstream of the humidity sensor in the exhaust system, wherein the predetermined operating condition is after a start of the internal combustion engine.

According to this preferred embodiment of the state determining apparatus for a humidity sensor, the adsorbent, made of zeolite or the like, capable of adsorbing hydrocarbons and moisture in exhaust gases is arranged in the exhaust system, and the humidity sensor is arranged downstream of the adsorbent. The adsorbent adsorbs hydrocarbon and moisture included in exhaust gases in relatively large amounts after the start of the internal combustion engine to prevent the hydrocarbons from being emitted to the atmosphere. In an initial stage after the start of the internal combustion engine, moisture is adsorbed by the adsorbent in a higher proportion and therefore passes through the adsorbent in a lower proportion, so that the humidity sensor detects a low humidity within a downstream exhaust pipe. Subsequently, as the moisture is incrementally adsorbed by the adsorbent, the moisture passes through the adsorbent in a higher proportion, causing the humidity to rise within the downstream exhaust pipe. In this manner, the humidity within the exhaust pipe detected by the humidity sensor largely increases after the start of the internal combustion engine, so that the characteristics and/or state of the humidity sensor, including the responsibility, can be appropriately and accurately determined by determining the state of the humidity sensor based on the change state parameter calculated during this period after the start. In addition, the adsorbent can be appropriately determined in terms of deterioration in accordance with the result of the determination.

Preferably, the state determining apparatus for a humidity sensor further comprises determination value setting means for setting a determination value in accordance with a responsibility of the humidity sensor before deterioration, wherein the state determining means compares the change state parameter with the set determination value to determine a degradation in the responsibility of the humidity sensor.

According to this preferred embodiment of the state determining apparatus for a humidity sensor, the change state parameter is compared with a determination value which is set in accordance with the responsibility of the humidity sensor before deterioration to determine a degradation in the responsibility of the humidity sensor. By thus comparing the determination value indicative of the responsibility before deterioration with the change state parameter, it is possible to more appropriately and accurately determine a degradation in the responsibility of the humidity sensor.

Preferably, in the state determining apparatus for a humidity sensor, the responsibility before deterioration is previously detected for each humidity sensor, and responsibility information indicative of the detected responsibility before deterioration is stored in the humidity sensor, and the determination value setting means sets the determination value based on the stored responsibility information.

According to this preferred embodiment of the state determining apparatus for a humidity sensor, the responsibility information indicative of the responsibility before deterioration previously detected for each the humidity sensor is stored in each humidity sensor, so that the determination value is set based on the responsibility information. It is therefore possible to appropriately set the determination value indicative of the responsibility before deterioration, while reflecting variations in the responsibility inherently possessed by the humidity sensor as an individual difference to the determination value, thereby more accurately determine a degradation in the responsibility of each humidity sensor.

DETAILED DESCRIPTION OF THE EMBODIMENT

Figure 1:
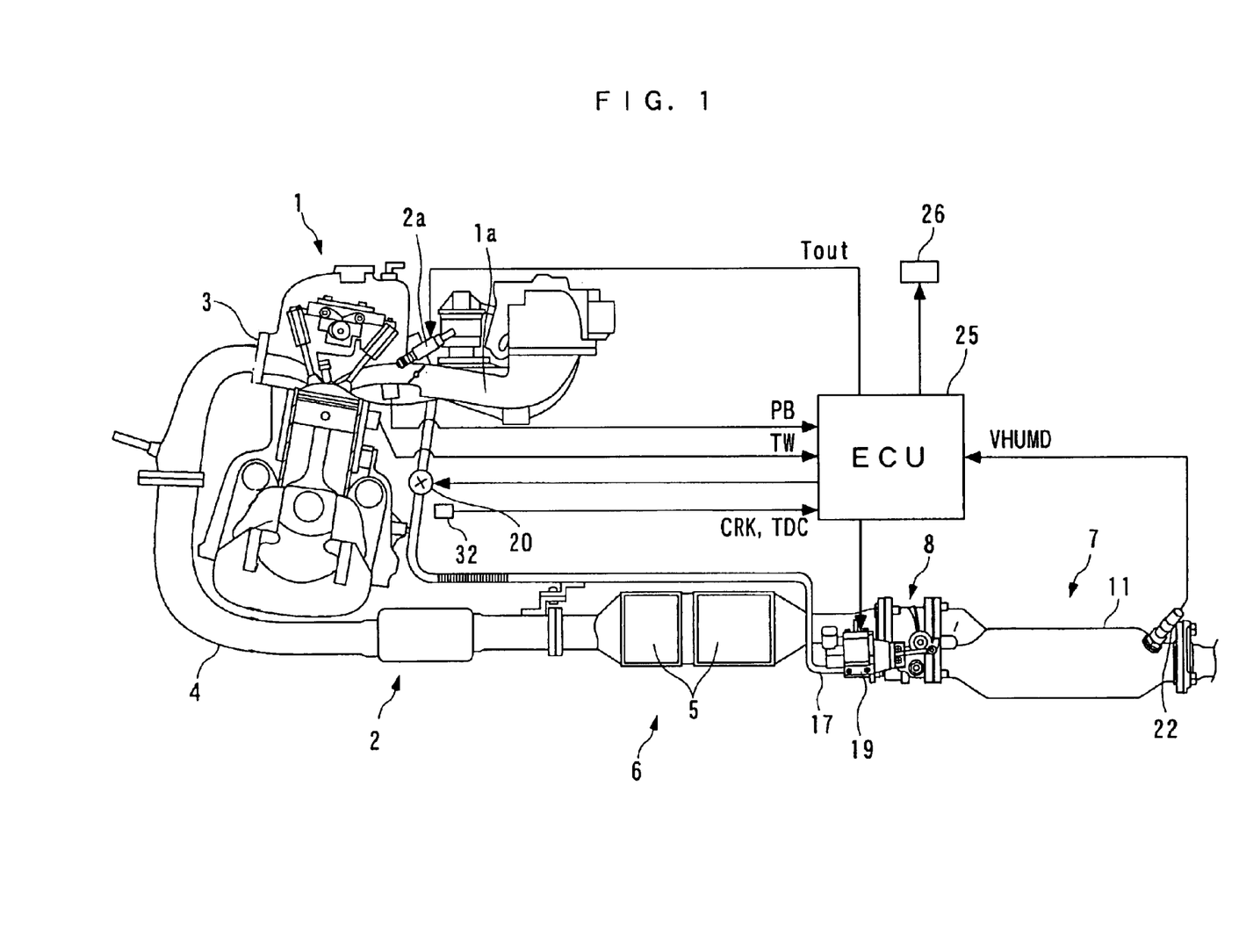
FIG. 1 is a diagram generally illustrating an internal combustion engine in which a state determining apparatus for a humidity sensor is applied according to one embodiment of the present invention.

In the following, a state determination apparatus for a humidity sensor according to a preferred embodiment of the present invention will be described in detail with reference to the accompanying drawings. FIG. 1 illustrates an internal combustion engine in which a state determining apparatus for a humidity sensor is applied according to the embodiment of the present invention. The illustrated internal combustion engine (hereinafter referred to as the "engine") 1 has an exhaust system 2 which includes an exhaust pipe 4 connected to the engine 1 through an exhaust manifold 3. A catalyzer 6 having two three-way catalysts 5, and a hydrocarbon adsorber 7 for adsorbing hydrocarbons are provided halfway in the exhaust pipe 4 for purifying exhaust gases. The two three-way catalysts 5 of the catalyzer 6 are arranged adjacent to each other along the exhaust pipe 4, and purify harmful substances (hydrocarbons (HC), carbon monoxide (CO) and nitrogen oxides (NOx)) in exhaust gases passing through the catalyzer 6 by oxidation-reduction catalyst actions, when they are heated to a predetermined temperature (for example, 300° C.) or higher and activated.

Figure 2:
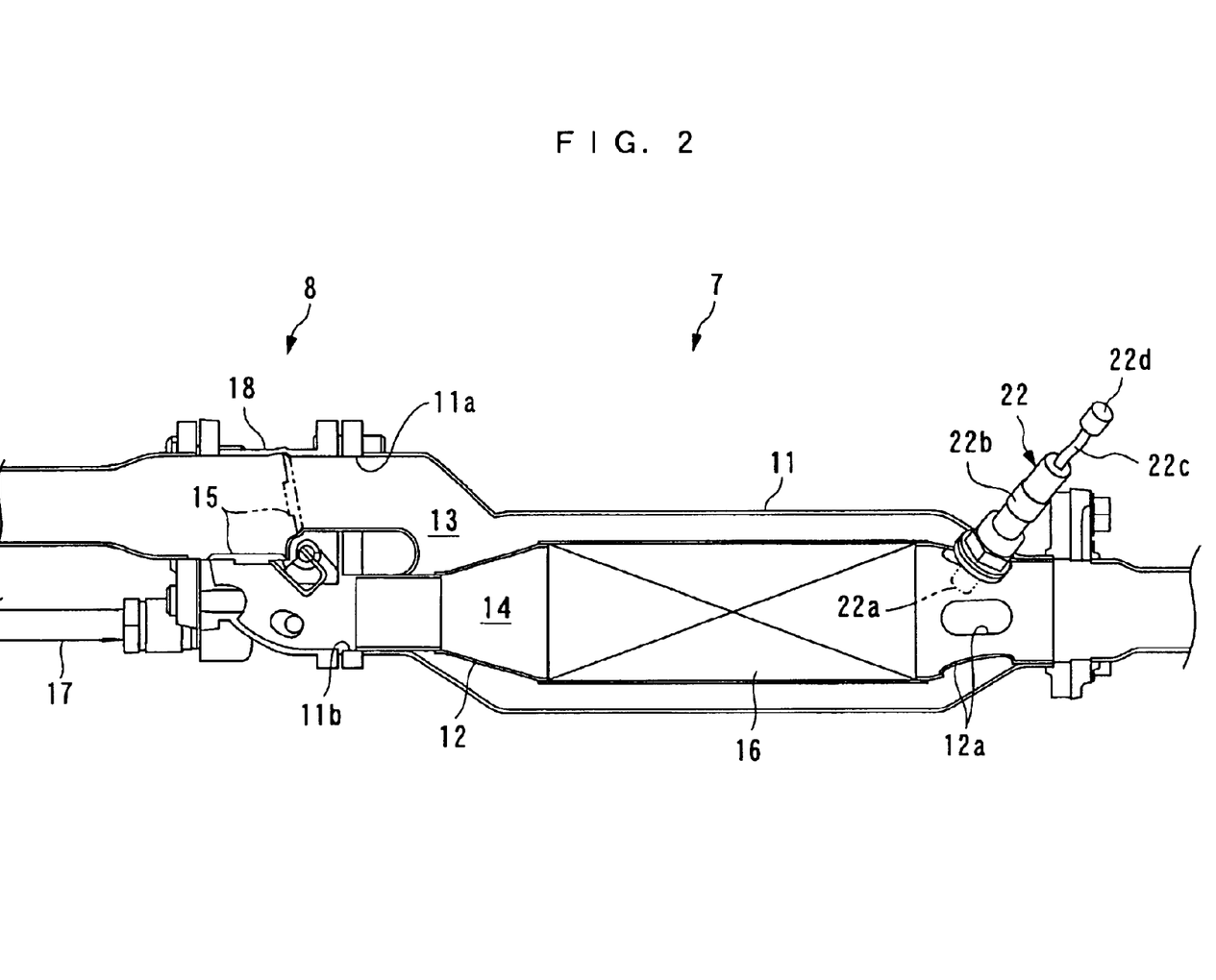
FIG. 2 is an enlarged cross-sectional view illustrating a hydrocarbon adsorber.

The hydrocarbon adsorber 7 in turn is arranged at a location downstream of the catalyst 6 in the exhaust pipe 4, and provided for reducing the amount of hydrocarbons emitted to the atmosphere by adsorbing hydrocarbons in exhaust gases during a starting period (for example, for approximately 30 to 40 seconds from the start) of the engine 1 in a cold state in which the three-way catalysts 5 have not been activated. As illustrated in FIGS. 1 and 2, the hydrocarbon adsorber 7 is coupled to an downstream end of the catalyzer 6 through an exhaust passage switch 8. The hydrocarbon adsorber 7 comprises a substantially cylindrical case 11; a bypass exhaust pipe 12 arranged within the case 11; and a cylindrical adsorbent 16 arranged halfway in the bypass exhaust pipe 12 for adsorbing hydrocarbons in exhaust gases which are introduced into the bypass exhaust pipe 12.

As illustrated in FIG. 2, the case 11 has its upstream end divided into two, i.e., an upper and a lower opening 11a, 11b. The upper opening 11a is in communication with a main passage 13 having an annular cross section and formed between the case 11 and bypass exhaust pipe 12, while the lower opening 11b is in communication with a bypass passage 14 which is an inner space of the bypass exhaust pipe 12.

The bypass exhaust pipe 12 has its upstream end connected to an inner surface of the lower opening 11b of the case 11, and a downstream end connected to an inner surface of a downstream end of the case 11, respectively, in an air tight state. The bypass exhaust pipe 12 is formed with a plurality (for example, five) of elongated communication holes 12a in a downstream end portion in the circumferential direction at equal intervals, such that the downstream end of the main passage 13 is in communication with the downstream end of the bypass passage 14 through these communication holes 12a.

The adsorbent 16 is comprised of a honeycomb core (not shown), made of a metal, which carries zeolite on its surface, and has the property of adsorbing moisture as well as hydrocarbons. As exhaust gases introduced into the bypass passage 14 pass through the adsorbent 16, hydrocarbons and moisture in the exhaust gases are adsorbed by the zeolite. The zeolite, which has high heat resistant properties, adsorbs hydrocarbons at low temperatures (for example, below 100° C.), and desorbs hydrocarbons once adsorbed thereby at a predetermined temperature or higher (for example, 100–250° C.). Then, the desorbed hydrocarbons are recirculated to the engine 1 from the hydrocarbon adsorber 7 through an EGR pipe 17 and an intake pipe 1a, and burnt by the engine 1.

The exhaust passage switch 8 is provided for selectively switching the passage of exhaust gasses downstream of the catalyzer 6 to the main passage 13 or bypass passage 14 in accordance with an activated state of the three-way catalysts 5. The exhaust passage switch 8 comprises a substantially cylinder coupling pipe 18; and a pivotable switching valve 15 arranged in the coupling pipe 18. The switching valve 15 is driven by a switching valve driver 19 (see FIG. 1) which is controlled by an ECU 25, later described, for switching the exhaust gas passage to the main passage 13 when it is present at a position indicated by solid lines in FIG. 2 and for switching the exhaust gas passage to the bypass passage 14 when it is present at a position indicated by two-dot chain lines.

As described above, the EGR pipe 17 is coupled between the coupling pipe 18 and the intake pipe 1a of the engine 1 for recirculating a portion of exhaust gases to the engine 1, and an EGR control valve 20 is arranged halfway in the EGR pipe 17. The EGR control valve 20 is controlled by the ECU 25 to actuate and stop the EGR and control an EGR amount.

In the foregoing configuration, the exhaust gas passage is switched to the bypass passage 14 by the exhaust passage switch 8 immediately after a cold start of the engine 1, thereby leading exhaust gasses passing through the catalyzer 6 to the bypass passage 14. The exhaust gases are emitted to the atmosphere after hydrocarbons in the exhaust gases have been adsorbed by the adsorbent 16. Subsequently, as it is determined that hydrocarbons have been adsorbed by adsorbent 16, the exhaust gas passage is switched to the main passage 13 to lead the exhaust gases to the main passage 13 through the coupling pipe 18 for emission to the atmosphere. Also, as the EGR control valve 20 is opened to operate the EGR, a portion of the exhaust gases is recirculated to the intake pipe 1a through the bypass passage 14 and EGR pipe 17 as an EGR gas. Hydrocarbons desorbed from the adsorbent 16 are sent to the intake pipe 1a by the EGR gas and burnt by the engine 1.

Figure 8:
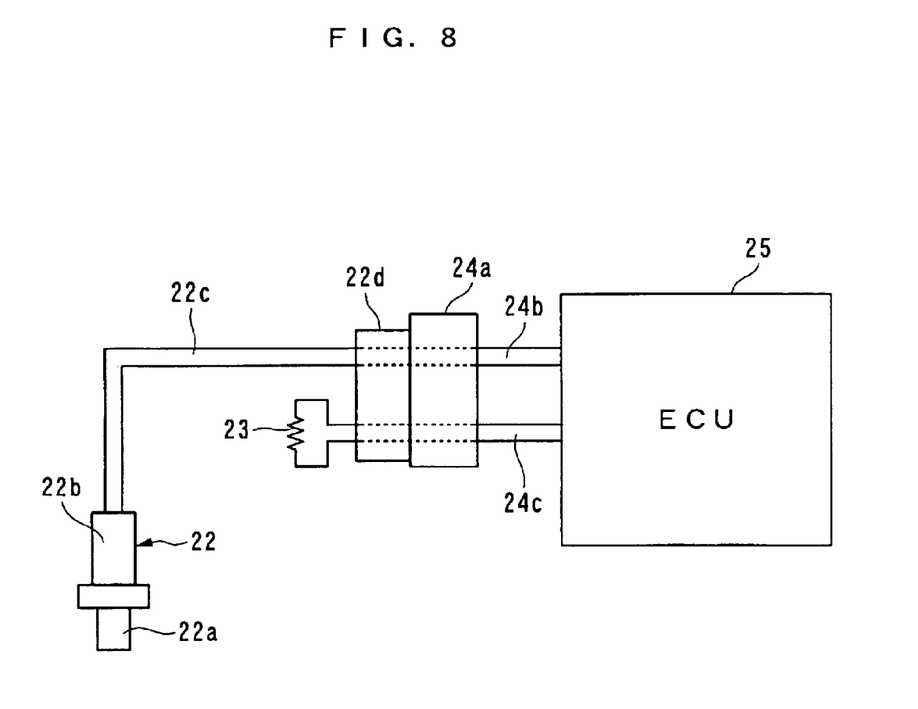
FIG. 8 is a diagram illustrating the configuration of the humidity sensor including a label resistive element.

A humidity sensor 22 is attached to the case 11 of the hydrocarbon adsorber 7 at a location downstream of the adsorbent 16. As illustrated in FIG. 2, the humidity sensor 22 comprises a sensor element 22a; a body 22b for attaching the sensor element 22a to face within the case 11; a harness 22c extending from the body 22b; and a coupler 22d connected to the leading end of the harness 22c. As illustrated in FIG. 8, the coupler 22d is connected to the ECU 25 through another coupler 24a and harnesses 24b, 24c. The sensor element 22a comprises a porous body, for example, made of alumina, titania or the like. The humidity sensor 22 takes advantage of the characteristic that its resistance value varies in accordance with the amount of moisture adsorbed into pores of the sensor element 22a to detect the humidity. In this embodiment, a relative humidity VHUMD corrected for the temperature, after converting a resistive partial potential (voltage) VR associated with the resistance value of the sensor element 22a, is outputted to the ECU 25 through the harness 24b as a detection signal of the humidity sensor 22.

Also, as illustrated in FIG. 8, a label resistive element 23 (responsibility information) is provided in the coupler 22d of the humidity sensor 22. The label resistive element 23 stores responsibility information before deterioration of the humidity sensor 22 by previously detecting the output characteristic of each humidity sensor 22 (the slope of an output value to an actual relative humidity) before use (before deterioration), determining which of a predetermined plurality (for example, ten) of output characteristic patterns the detected output characteristic falls under, and providing the coupler 22d with a resistive element having the resistance value corresponding to the determined output characteristic pattern. The label resistive element 23 is connected to the ECU 25 through the coupler 24a and harness 24c, so that the resistance value is read by the ECU 25 as a label resistance value Rn (for example R1–R10) (responsibility information). It should be noted that the label resistive element 23 is arranged in the coupler 22d because the coupler 22d will not be heated unlike the body 22b which is in contact with the exhaust system 2 of the engine 1.

The ECU 25 also receives a signal indicative of an engine water temperature TW from an engine water temperature sensor 23; a signal indicative of an intake pipe inner pressure PB from an intake pipe inner pressure sensor 24; and a CRK signal, which is a pulse signal, from a crank angle sensor 32, respectively. The CRK signal is generated every predetermined crank angle as a crack shaft, not shown, of the engine 1 is rotated. The ECU 25 calculates a rotational speed NE of the engine 1 based on the CRK signal. An alarm lamp 26 is further connected to ECU 25 for generating an alarm by lighting when it is determined that the absorbent 16 or humidity sensor 22 is deteriorated.

In this embodiment, the ECU 25 functions as an operating condition determining means, change state parameter calculating means, state determining means, and determination value setting means. The ECU 25 is based on a microcomputer which comprises an I/O interface, a CPU, a RAM, a ROM and the like. The detection signals from the aforementioned sensors such as the humidity sensor 22 are inputted to the CPU after they are respectively A/D converted and reshaped in the I/O interface. The CPU controls a fuel injection time Tout for an injector 2a of the engine 1, the switching valve driver 19, and the EGR control valve 20 in accordance with a control program and the like stored in the ROM in response to the foregoing detection signals, and determines deteriorations of the adsorbent 16 and humidity sensor 22.

The adsorbent 16 is determined as to whether or not it is deteriorated based on the relative humidity VHUMD detected by the humidity sensor 22 during adsorption of the humidity 16 after the start of the engine 1. Specifically, for example, as described in the aforementioned Japanese Patent Application No. 2000-338375, a measurement is made on a time required for the relative humidity VHUMD to rise by a predetermined value, and the adsorbent 16 is determined as deteriorated when the measured time is shorter than a predetermined time because the relative humidity VHUMD rises at a high rate.

Figure 3:
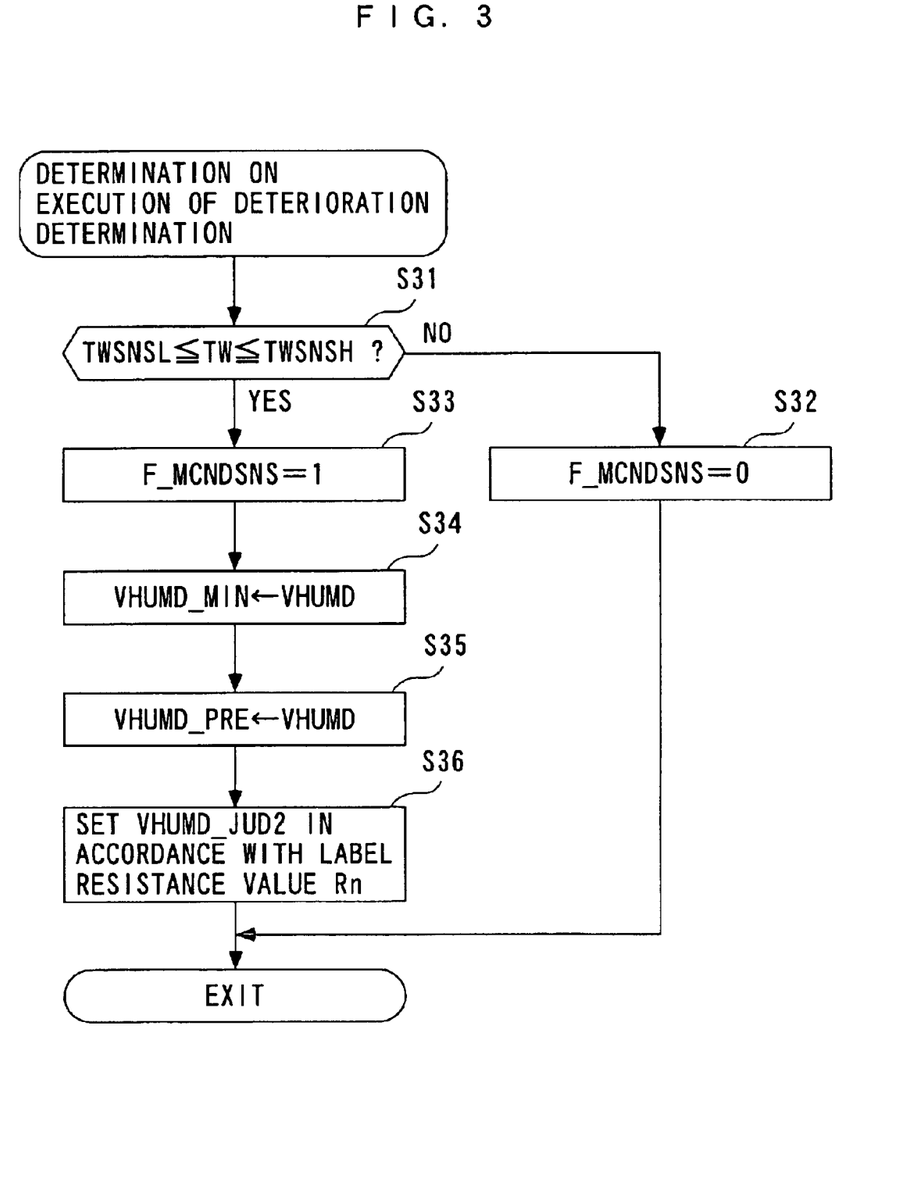
FIG. 3 is a flow chart illustrating a routine for determining whether or not a deterioration determination is executed for a humidity sensor.

Next, processing for determining a deterioration of the humidity sensor 22 will be described with reference to FIGS. 3 to 5. FIG. 3 illustrates a routine for determining whether or not a deterioration determination is executed for the humidity sensor 22. This routine is executed only once immediately after the engine 1 is started.

First, in this routine, it is determined at step 31 (labeled as "S31" in the figure. The same applies to the following description) whether or not the engine water temperature TW is equal to or higher than a lower limit value TWSNSL (for example, 0° C.) and equal to or lower than an upper limit value TWSNSH (for example, 50° C.). If the answer to step 31 is NO, i.e., when the engine water temperature TW at the start is out of a predetermined range defined by the upper and lower limit values TWSNSL, TWSNSH, the ECU 25 sets a deterioration determination enable flag F_MCNDSNS to "0" (step 32) on the assumption that conditions are not met for executing a deterioration determination for the humidity sensor 22, followed by termination of this routine.

On the other hand, if the answer to step 31 is YES, i.e., when the engine water temperature TW is within the predetermined range, the ECU 25 sets the deterioration determination enable flag F_MCNDSNS to "1" (step 33) on the assumption that the conditions are met for executing the deterioration determination for the humidity sensor 22. Next, the ECU 25 sets the relative humidity VHUMD detected by the humidity sensor 22 at that time as initial values of a minimum value VHUMD_MIN and a previous value VHUMD_PRE, respectively, of the relative humidity (steps 34, 35).

Next, the ECU 25 sets a deterioration determination value VHUMD_JUD2 (determination value), later described, in accordance with a label resistance value Rn (responsibility information) read from the label resistive element 23 of the humidity sensor 22 (step 36), followed by termination of this routine. As described above, the label resistance value Rn indicates the responsibility of the humidity sensor 22 before deterioration, so that the deterioration determination value VHUMD_JUD2 can be appropriately set for each sensor through the execution of step 36, while reflecting variations in responsibility inherently possessed by each humidity sensor 22 as an individual difference to the deterioration determination value VHUMD_JUD2.

Figure 4:
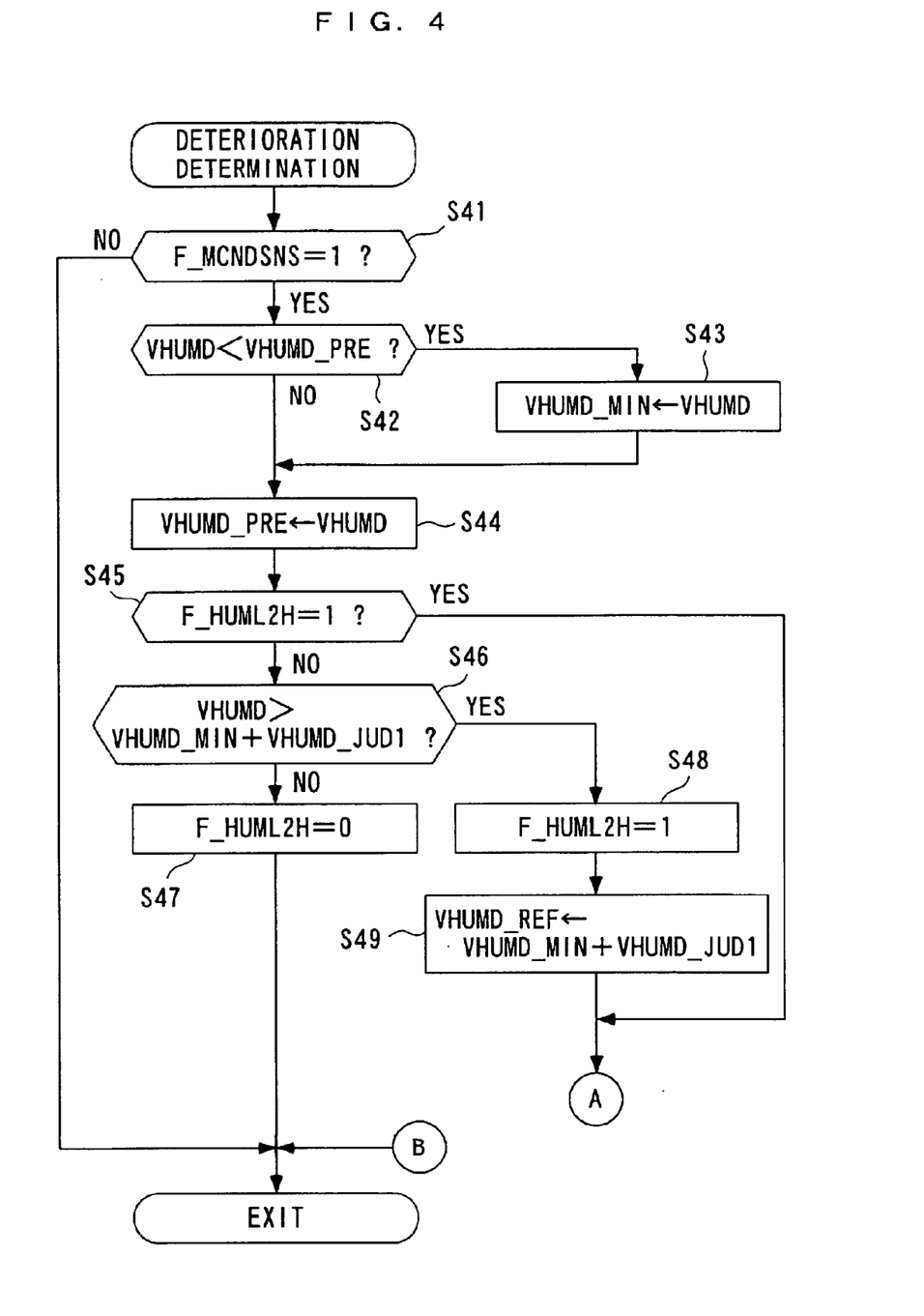
FIGS. 4 and 5 are flow charts illustrating in combination a routine for determining a deterioration of the humidity sensor.
Figure 5:
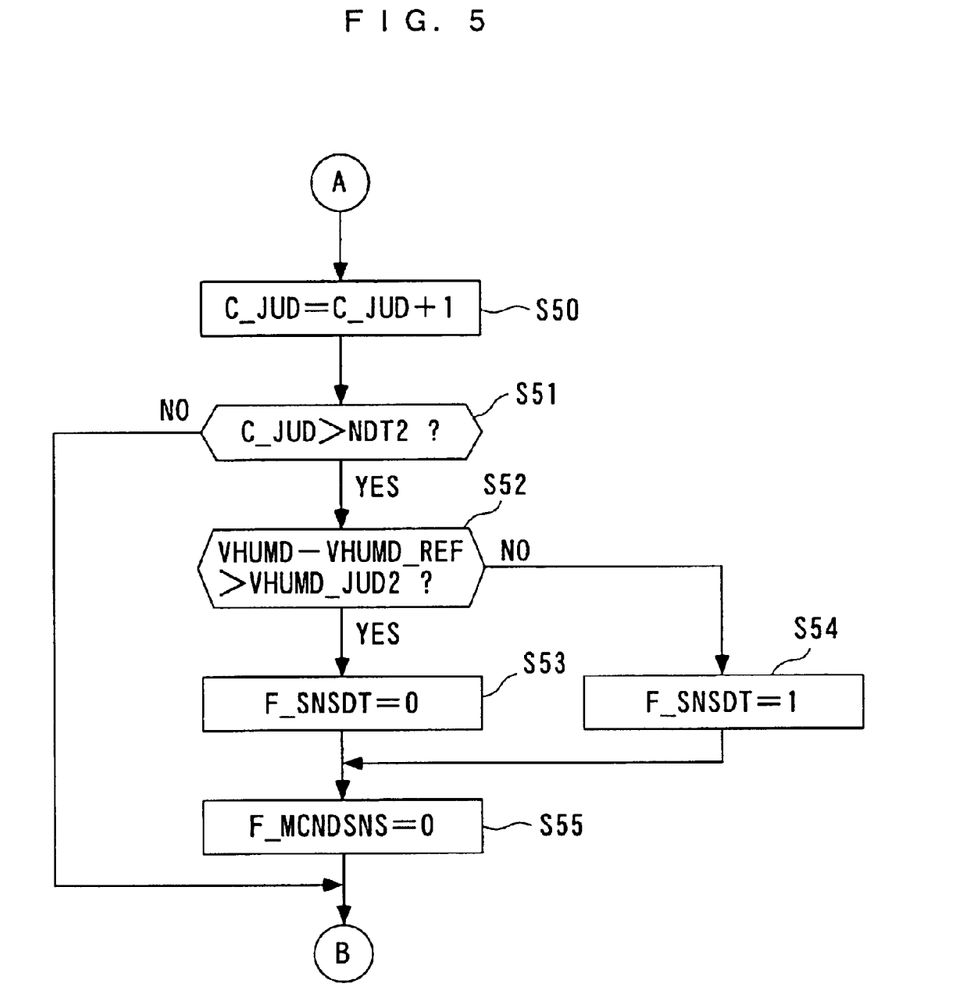

FIGS. 4 and 5 illustrate a routine for determining a deterioration of the humidity sensor 22 in accordance with the result of the determination made by the routine of FIG. 3. This routine is executed every predetermined time (for example, 100 ms). It is first determined whether or not the deterioration determination enable flag F_MCNDSNS is "1" (step 41). If the answer to step 41 is NO, i.e., when conditions are not met for executing the deterioration determination, this routine is terminated without further processing.

Figure 6:
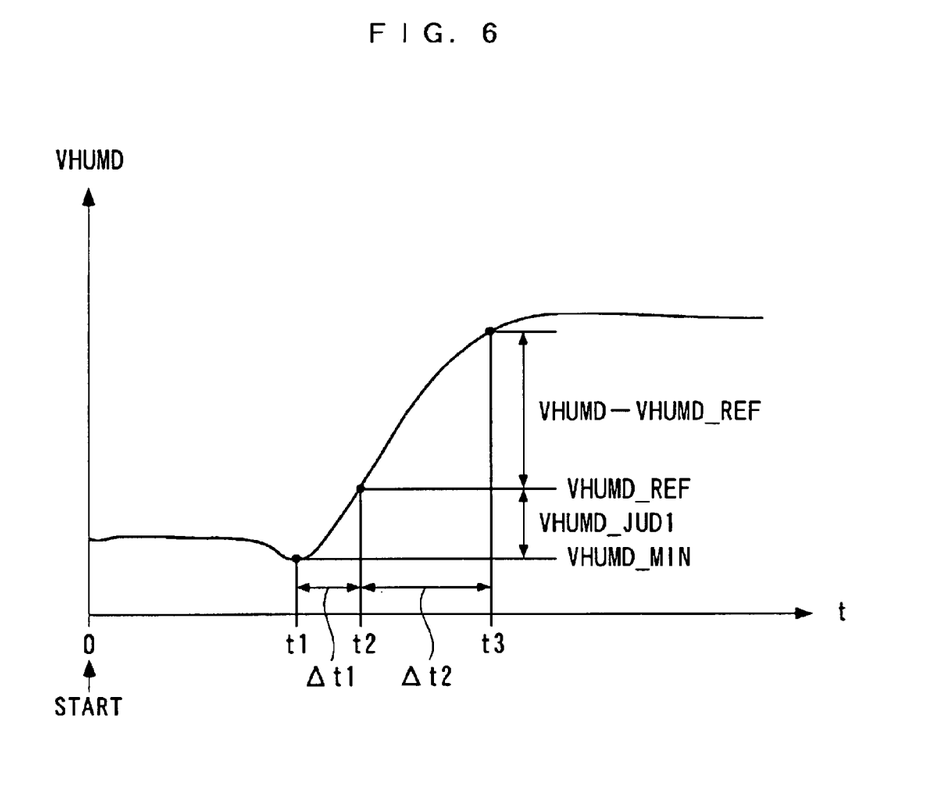
FIG. 6 is a timing chart showing an example of applying the deterioration determination processing according to the embodiment.

On the other hand, if the answer to step 41 is YES, i.e., the conditions are met for executing the deterioration determination, it is determined whether or not the relative humidity VHUMD detected at this time by the humidity sensor 22 is lower than the previous value VHUMD_PRE (step 42). If the answer to step 42 is YES, i.e., when VHUMD<VHUMD_PRE, the relative humidity VHUMD at that time is set as the minimum value VHUMD_MIN (step 43). In this manner, the minimum value VHUMD_MIN is updated anytime when the relative humidity VHUMD is lower than that detected at the last time, so that the minimum value VHUMD_MIN indicates a minimum value of the relative humidity VHUMD detected by the humidity sensor 22 after the start of the engine 1 (for example, at time t1 in FIG. 6). If the answer to step 42 is NO, or after executing step 43, the routine proceeds to step 44, where the ECU 25 shifts the current relative humidity VHUMD to the previous value VHUMD_PRE.

It is next determined whether or not a rising establishment flag F_HUML2H is "1" (step 45). If the answer to step 45 is NO, it is determined whether or not the relative humidity VHUMD is larger than the sum of the minimum value VHUMD_MIN and a predetermined rising determination value VHUMD_JUD1 (for example 10%) (step 46). If the answer to step 46 is NO, the ECU 25 sets the rising establishment flag F_HUML2H to "0" on the assumption that the relative humidity VHUMD has not yet sufficiently risen (step 47), followed by termination of this routine.

On the other hand, if the answer to step 46 is YES, showing that VHUMD>VHUMD_MIN+VHUMD_JUD1 is established, i.e., when the relative humidity VHUMD has increased from the minimum value VHUMD_MIN by the rising determination value VHUMD_JUD1 or more (at time t2 in FIG. 6), the ECU 25 sets the rising establishment flag F_HUML2H to "1" (step 48) on the assumption that the relative humidity VHUMD has sufficiently risen and is now stably rising. Next, the ECU 25 sets the sum of the minimum value VHUMD_MIN and rising determination value VHUMD_JUD1 to a reference value VHUMD_REF (step 49), followed by the routine proceeding to step 50 onward in FIG. 5. Also, after the ECU 25 sets the rising establishment flag F_HUML2H to "1" at step 48, the answer to step 45 is YES, in which case the routine directly proceeds to step 50 onward.

At step 50, the ECU 25 increments a counter C_JUD. It is next determined whether or not the count value exceeds a predetermined value NDT2 (corresponding to a predetermined time Δt2 (for example, one second) in FIG. 6) (step 51). If the answer to step 51 is NO, this routine is terminated.

On the other hand, if the answer to step 51 is YES, showing that C_JUD>NDT2, i.e., when the predetermined time Δt2 has elapsed after the establishment of the rise of the relative humidity VHUMD (at time t3 in FIG. 6), it is determined whether or not the difference between the relative humidity VHUMD at that time and the reference value VHUMD_REF set at step 49 (=VHUMD−VHUMD_REF) (change state parameter) is larger than the sum of the relative humidity VHUMD and the deterioration determination value VHUMD_JUD2 set at step 36 (step 52).

If the answer to step 52 is YES, i.e., when the relative humidity VHUMD is rising beyond the deterioration determination value VHUMD_JUD2 during the predetermined time Δt2 after the rise of the relative humidity VHUMD, the ECU 25 determines that the humidity sensor 22 is not deteriorated on the assumption that the relative humidity VHUMD is changing at a high rate and the humidity sensor 22 maintains a good responsibility, and sets a deterioration flag F_SNSDT to "0" for indicating this fact (step 53).

On the other hand, if the answer to step 52 is NO, i.e., when the relative humidity VHUMD increases by the deterioration determination value VHUMD_JUD2 or less during the predetermined time Δt2, the ECU 25 determines that the humidity sensor 22 is deteriorated on the assumption that the relative humidity VHUMD is changing at a low rate and the humidity sensor 22 exhibits a lower responsibility, and sets the deterioration flag F_SNSDT to "1" (step 54).

At step 55 subsequent to step 53 or 54, the ECU 25 sets the deterioration determination enable flag F_MCNDSNS to "0" in response to the termination of the deterioration determination for the humidity sensor 22, followed by termination of this routine.

As described above, according to the foregoing embodiment, an increase in the relative humidity VHUMD (VHUMD−VHUMD_REF) during the predetermined time Δt2 is compared with the deterioration determination value VHUMD_JUD2 based on the relative humidity VHUMD detected by the humidity sensor 22 while the humidity of exhaust gases is increasing at a location downstream of the adsorbent 16 during adsorption by the adsorbent 16 after the start of the engine 1, so that the state of the humidity sensor 22 can be appropriately and accurately determined, including a degradation in responsibility. In addition, a deterioration determination can be appropriately made for the adsorbent 16 in accordance with the result of the determination.

Also, since the deterioration determination value VHUMD_JUD2 is set in accordance with the label resistance value Rn indicative of the responsibility information before deterioration of the humidity sensor 22, the responsibility degradation can be determined for each sensor with a high accuracy while reflecting variations in the responsibility inherently possessed by the humidity sensor 22 as an individual difference to the deterioration determination value VHUMD_JUD2. In this event, the deterioration determination value VHUMD_JUD2 may be fixed, and the predetermined time Δt2 may be set in accordance with the label resistance value Rn, thereby providing similar advantages.

Further, the time at which the relative humidity VHUMD has increased from the minimum value VHUMD_MIN after the start by the rising determination value VHUMD_JUD1 is defined as a rising time of the relative humidity VHUMD, and the predetermined time Δt2 is measured from this time, so that the relative humidity VHUMD detected when the relative humidity VHUMD has sufficiently risen and is stably increasing can be used in the determination, and accordingly the degradation determination can be more accurately made for the responsibility of the humidity sensor 22. Though not shown, the determination on the rising establishment by the rising determination value VHUMD_JUD1 may be omitted, in which case the predetermined time Δt2 may be a time from the time at which the minimum value VHUMD_MIN is generated.

Figure 7:
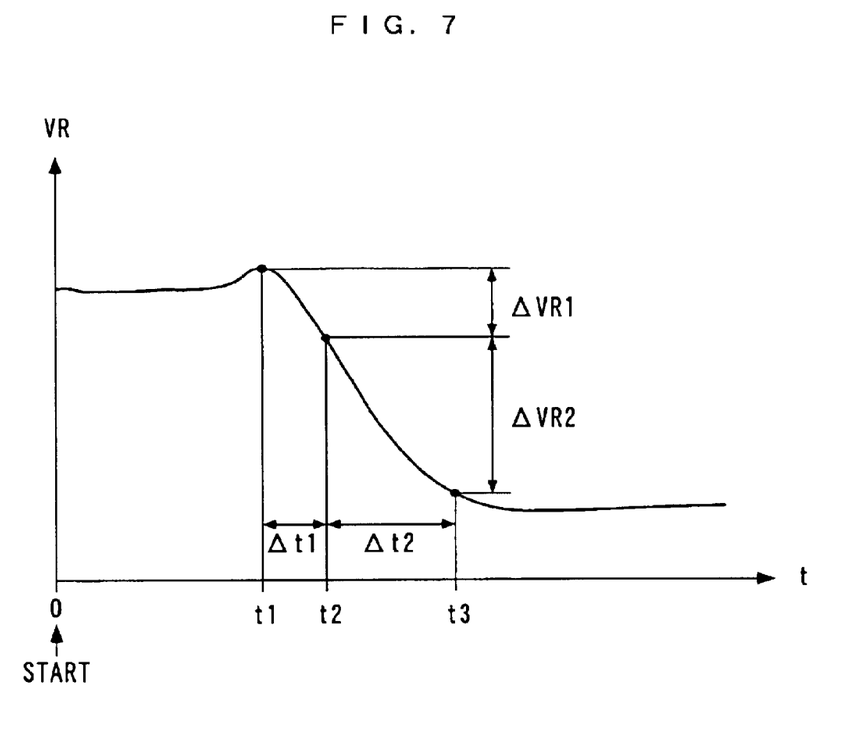
FIG. 7 is a timing chart showing an example of applying the deterioration determination processing according to an exemplary modification to the embodiment.

FIG. 7 illustrates an exemplary modification to the foregoing embodiment. In this modification, the detection signal of the humidity sensor 22 is taken out without converting the resistive partial potential VR of the sensor element 22a. Therefore, the resistive partial potential VR presents a higher value because a lower humidity of exhaust gases causes the sensor element 22a to have a larger resistance value. In other words, the resistive partial potential VR presents completely reverse behaviors to the relative humidity VHUMD in the foregoing embodiment in terms of the magnitude and increase/decrease. Therefore, completely the same determination can be made based on the resistive partial potential VR which is the value detected by the humidity sensor 22, as is the case with the aforementioned relative humidity VHUMD.

Describing in brief, a maximum value of the resistive partial potential VR is calculated while updating (at time t1) after the start of the engine 1. A time (time t2) at which the resistive partial potential VR has decreased from the maximum value by a fall determination value ΔVR1 is defined as a fall establish time. A reduction ΔVR2 (change state parameter) of the resistive partial potential VR from the time t2 to a time (t3) at which the predetermined time Δt2 has elapsed is compared with a predetermined determination value (determination value). In this manner, the state of the humidity sensor 22 including a degradation in responsibility can be appropriately and accurately determined.

It should be understood that the present invention is not limited to the embodiment described above, but may be practiced in a variety of forms. For example, in the foregoing embodiment, the predetermined time Δt2 is basically fixed, and an increase (VHUMD−VHUMD_REF) in the relative humidity VHUMD and a reduction ΔVR2 in the resistive partial potential VR during the predetermined time Δt2 are used as direct change state parameters. Alternatively, this relationship may be reversed. Specifically, the increase in the relative humidity VHUMD or the reduction in the resistive partial potential VR may be a predetermined value, and a time required to reach the predetermined value may be used as a direct change state parameter which may be compared with a predetermined time set therefor.

Also, the foregoing embodiment employs an increase in the relative humidity VHUMD and a reduction ΔVR2 in the resistive partial potential VR during the predetermined time Δt2, i.e., the changing rates (average slopes) of the detection values as the change state parameters for the detection value of the humidity sensor 22. Instead of this, other appropriate parameters may be employed. For example, an acceleration of a change in a detection value may be calculated at all times as a change state parameter, and a maximum value of the calculated changing acceleration may be compared with a determination value set therefor. Otherwise, details in configuration can be modified as appropriate without departing from the spirit and scope of the invention set forth in the appended claims.

As described above in detail, the state determination apparatus for a humidity sensor according to the present invention can advantageously determine with a high accuracy the state of the humidity sensor, including the responsibility thereof, from a result detected by the sensor itself.

What is claimed is:

1. An apparatus for determining a deterioration of a humidity sensor arranged in an exhaust system of an internal combustion engine for detecting a humidity within an exhaust pipe, said apparatus comprising:

operating condition determining means for determining whether or not said internal combustion engine is in a predetermined operating condition;

change state parameter calculating means for calculating a change state parameter indicative of a change state of a value detected by said humidity sensor based on the detected value of said humidity sensor detected when said internal combustion engine is in said predetermined operating condition; and deterioration determining means for determining the deterioration of said humidity sensor in accordance with said calculated change state parameter.

2. A deterioration determining apparatus for a humidity sensor according to claim 1, further comprising:

an adsorbent capable of adsorbing hydrocarbons and moisture in exhaust gases, said adsorbent being arranged at a location upstream of said humidity sensor in said exhaust system, wherein said predetermined operating condition is after a start of said internal combustion engine.

3. A deterioration determining apparatus for a humidity sensor according to claim 1, further comprising:

determination value setting means for setting a determination value in accordance with a responsibility of said humidity sensor before deterioration, wherein said deterioration determining means compares said change state parameter with said set determination value to determine a degradation in the responsibility of said humidity sensor.

4. A deterioration determining apparatus for a humidity sensor according to claim 3, wherein:

said responsibility before deterioration is previously detected for said humidity sensor, and responsibility information indicative of the detected responsibility before deterioration is stored in said humidity sensor, and said determination value setting means sets said determination value based on said stored responsibility information.

* * * * *